(12) United States Patent
Lonky et al.

(10) Patent No.: US 6,258,044 B1
(45) Date of Patent: *Jul. 10, 2001

(54) APPARATUS AND METHOD FOR OBTAINING TRANSEPITHELIAL SPECIMEN OF A BODY SURFACE USING A NON-LACERATING TECHNIQUE

(75) Inventors: Neal M. Lonky, Yorba Linda, CA (US); Jeremy James Michael Papadopoulos, Milwaukee, WI (US)

(73) Assignee: Oralscan/Trylon Joint Venture, Suffern, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/360,425

(22) Filed: Jul. 23, 1999

Related U.S. Application Data
(60) Provisional application No. 60/093,910, filed on Jul. 23, 1998.

(51) Int. Cl.[7] .................................................. A61B 10/00
(52) U.S. Cl. ........................................... 600/569; 600/562
(58) Field of Search ..................................... 600/562, 569, 600/570; 604/1; 606/161; 15/DIG. 6, 206, 207.2

(56) References Cited

U.S. PATENT DOCUMENTS

| | | | |
|---|---|---|---|
| 2,675,572 | * 4/1954 | Nomiya | 15/164 |
| 2,839,049 | 6/1958 | MacLean | 600/569 |
| 2,955,591 | 10/1960 | MacLean | 600/569 |
| 4,227,537 | * 10/1980 | Suciu et al. | 600/569 |
| 4,759,376 | * 7/1988 | Stormby | 128/756 |
| 4,873,992 | * 10/1989 | Bayne | 600/569 |
| 5,067,195 | * 11/1991 | Sussman | 15/167.001 |
| 5,184,626 | 2/1993 | Hicken | 600/569 |
| 5,257,182 | 10/1993 | Luck et al. | 382/224 |
| 5,623,941 | * 4/1997 | Hedberg et al. | 600/569 |
| 5,713,369 | * 2/1998 | Tao et al. | 600/569 |
| 5,761,760 | * 6/1998 | Dumler et al. | 15/206 |
| 5,937,870 | * 8/1999 | Gueret | 132/218 |

* cited by examiner

*Primary Examiner*—Cary O'Conner
*Assistant Examiner*—Charles Marmor, II
(74) *Attorney, Agent, or Firm*—Levisohn, Lerner, Berger & Langsam

(57) ABSTRACT

A non-lacerational technique to collect cells in an oral mouth cavity utilizes a brush with bristles which have an abrading surface and collect cells from the superficial, intermediate and basal layers of the oral tissue.

39 Claims, 8 Drawing Sheets

APPARATUS AND METHOD FOR OBTAINING TRANSEPITHELIAL SPECIMEN OF A BODY SURFACE USING A NON-LACERATING TECHNIQUE

This application claims the priority of U.S. provisional application Ser. No. 60/093,910 filed Jul. 23, 1998.

FIELD OF THE INVENTION

The present invention is directed to a method and apparatus for obtaining transepithelial specimens of body surfaces using a non-lacerating technique. Specifically, the invention is directed to tools for sampling squamous epithelium from lesions found in the oral cavity and in similar body tissues. The invention is also directed to an improved method of testing all lesions that involve the epithelium of the oral cavity and/or similar body tissues.

BACKGROUND OF THE INVENTION

Cancers of the oral cavity and pharynx are a major cause of death from cancer in the U.S., exceeding the U.S. death rates for cervical cancer, malignant melanoma and Hodgkin's disease. According to the American Cancer Society's Department of Epidemiology and Surveillance, an estimated 30,750 new cases of oral cancer were diagnosed in the U.S. during 1997, a figure which accounts for 2% to 4% of all cancers diagnosed annually.

Despite advances in surgery, radiation, and chemotherapy, the mortality rate of oral cancer has not improved in the last 20 years. Ultimately, 50% of patients die from their malignancy, and 8,440 U.S. deaths were predicted for 1997. There are several reasons for the high mortality rate from oral cancer, but undoubtedly, the most significant factor is delayed diagnosis. Studies have demonstrated that the survival and cure rate increase dramatically when oral cancer is detected at an early stage. For example, the 5-year survival rate for patients with localized disease approximates 79% compared to 19% for those with distant metastases. Unfortunately, approximately two thirds of patients at time of diagnosis have advanced disease, and over 50% display evidence of spread to regional lymph nodes and distant metastases.

Delay in the diagnosis of oral cancer is often the result of the limited diagnostic tools available in the prior art. The dentist or physician who detects an oral lesion which is not clearly suggestive of a precancer or cancer clinically, and who is limited to the prior art tools and methods, is faced with a quandary. Approximately 5–10% of adult patients seen in a typical dental practice exhibit some type of oral lesion, yet only a small proportion (approximately 0.5% to 1%) are precancerous or cancerous. These oral lesions are commonly evidenced as a white or reddish patch, ulceration, plaque or nodule in the oral cavity. The overwhelming majority of these lesions are relatively harmless; however, the multitude of poorly defined lesions in the oral cavity can be confounding to the clinician. A diverse group of oral lesions may be easily confused with malignancy, and conversely, malignancy may be mistaken for a benign lesion. Benign tumors, reactive processes, traumatic lesions, oral manifestations or systemic diseases, inflammatory oral disorders, and bacterial, viral and fungal infections all display similar oral features thereby impeding establishment of an accurate clinical diagnosis.

The only reliable means currently available in the prior art to determine if a suspect oral lesion is pre-cancerous or cancerous, is to incise or excise (i.e. lacerate) the lesion surgically with either a scalpel or a laser so that a histological section of the removed tissue can be prepared for microscopic evaluation. Histology can be generally defined as the microscopic inspection or other testing of a cross section of tissue. This prior art form of oral surgical biopsy is generally performed by a surgeon, and is often inconvenient, painful, and expensive. Furthermore, since the greatest number of oral cancers develop on the lateral border of the tongue and floor of the mouth, the difficulty and potential complications of biopsying these lesions, including pain, bleeding, and scar formation, can be significant. Not infrequently, biopsy is delayed either by the patient due to fear of the procedure, or by the clinician due to technical difficulty in obtaining an adequate specimen.

Since the majority of oral abnormalities detected clinically prove benign when tested microscopically, and given the limitations of biopsy, including cost, inconvenience, pain and potential for complications, relatively few oral lesions are subjected to biopsy. It is primarily for this reason that only oral lesions with clinical features strongly suggestive of cancer or precancer are referred for biopsy as described in the prior art. As a result, many patients with ominous, but visually less suggestive lesions are allowed to progress to advanced oral cancer, with their condition undiagnosed and untreated.

In many body sites, but not the oral cavity, a technique known as cytology is commonly utilized as an alternative to performing a lacerating biopsy and histological evaluation. In these body sites, pre-cancerous and cancerous cells or cell clusters tend to spontaneously exfoliate, or "slough off" from the surface of the epithelium. These cells or cell clusters are then collected and examined under the microscope for evidence of disease.

Since prior-art cytology is directed towards the microscopic examination of spontaneously exfoliated cells, obtaining the cellular sample is generally a simple, non-invasive, and painless procedure. Exfoliated or shed cells can often be obtained directly from the body fluid which is contiguous with the epithelium. Urine can thus be examined for evidence of bladder cancer, and sputum for lung cancer. Alternatively, exfoliated or shed cells may be obtained by gently scraping or brushing the surface of a mucus membrane epithelium to remove the surrounding mucus using a spatula or soft brush. This is the basis for the well known procedure known as the Pap smear used to detect early stage cervical cancer.

Because of the ease by which a cellular sample can be obtained from these body sites, prior-art cytology is typically utilized to screen asymptomatic populations for the presence of early stage disease. In the cervical Pap smear, for example, the entire surface area of the cervical regions where cancer generally occurs is gently scraped or brushed to collect and test the mucus from those regions. Abrasion of the underlying cervical epithelium is undesired, as it can cause bleeding and discomfort to the patient. This procedure is thus typically performed when no particular part of the cervix appears diseased, and when no suspect lesion is visible.

The design of prior art cytology sampling instruments reflects their use to sweep up cells which were spontaneously exfoliated and present on the superficial epithelial surface. Since prior-art cytology brushes need only to gently remove surface material, they are designed of various soft materials which can collect the cervical mucous with minimal abrasion to the underlying epithelium. These cytology sampling instruments therefore either have soft bristles, soft flexible fimbriated or fringed ends, or even, as in the case of the cotton swab or spatula, no bristles at all.

Examples of prior art cytological sampling tools include the wooden, metal or plastic spatula. According to the traditional method of Pap smear sampling, the spatula is placed onto the surface of the cervix and lightly depressed or scraped across the surface of the cervix to pick up exfoliated cells.

Further examples of prior art cytological sampling tools include the Cytobrush®; a device which uses soft and tapered bristles to sample shed cells from the cervical canal. U.S. Pat. No. 4,759,376, which allegedly covers this product, likewise describes a conical tapered soft bristle brush (a mascara brush shape) which is placed into the cervical canal and rotated for endocervical sampling. U.S. Pat. No. 4,759,376 teaches that the bristles "are to be relatively soft such as that of a soft toothbrush to more readily bend and avoid damaging the tissues." By way of further example, physicians have long used the common swab, commercially known as the Q-Tip®, to perform endocervical sampling.

Other prior art cytological sampling tools designed to obtain a cytological sample from the cervix may combine both endocervical and exocervical sampling regions into one device. These devices swab the surface of mucous-covered tissue by soft brushing the mucous layer of the endocervix and exocervix at the same time, thereby collecting the cells contained in the mucous layer tissue of those surfaces. These devices include the Unimar®-Cervex Brush™, a brush that has a contoured flat comb-like head with a single layer of flexible plastic bristles (similar to a flat paint brush having only one row of bristles) in which the center bristles are longer than the bristles on the ends. According to the method of use for the device, the center bristles are inserted into the cervical canal until the lateral bristles bend against the exocervix. The device is then removed and the cells are swabbed across a microscope slide similar to painting with a paintbrush.

Similarly, the Bayne Pap Brush™, which Medical Dynamics, Inc. represents is covered by U.S. Pat. No. 4,762,133, contains a center arm, made of soft DuPont bristles, running horizontal to the cervical canal and a second arm of soft bristles at ninety degrees to the first arm, creating an L-shape. The center arm is placed within the cervical canal and then rotated. Upon rotation, the soft bristles of the second arm automatically sweep the surface of the exocervix in a circular motion thereby sampling the exocervix along with the endocervix.

Although cytology has been adopted for use in several other body sites, it has not been found useful to test questionable lesions of the oral cavity. This is in large part due to the fact that the prior art devices and methods used to obtain a cellular sample for cytology are unsatisfactory when used to sample lesions of the oral cavity and similar epithelia. Unlike the uterine cervix, questionable lesions of the oral cavity and similar epithelia may be typically coated with multiple layers of keratinized cells. This "keratin layer" forms a relatively hard "skin-like" coating over the surface of the lesion and may thus hide the abnormal cells lying underneath it and prevent their exfoliation from the surface.

As noted above, the design of prior art cytology sampling instruments reflect their use in tissues where spontaneously exfoliated abnormal cells are commonly present on the surface of an area of epithelium that harbors disease. These cytology sampling instruments therefore either have soft bristles, soft flexible fimbriated ends, or even no bristles at all. Since prior-art cytology brushes only need to gently remove surface material, they are designed of various soft materials which can collect the cervical mucous with minimal abrasion to the underlying epithelium.

While abnormal cells can spontaneously exfoliate to the epithelial surface and be gently removed by prior art instruments in the uterine cervix and other similar tissues, in many oral cavity lesions the abnormal cells never reach the surface because they are blocked by the keratin layer. This limitation is a major cause of the high false negative rate of prior art cytological testing to detect lesions of the oral cavity. That is, a large proportion of oral lesions found to be positive using lacerating biopsy and histology are found to be negative using cytology. In one major study, this false negative rate was found to be as high as 30%.

It is largely due to this lack of correlation between histology and prior art oral cytology that there is currently no significant use of oral cytology in the United States or elsewhere to test questionable oral lesions. Since it is well known that dangerous, truly cancerous oral lesions may commonly be reported as "negative" using prior art cytologic sampling techniques, prior art cytologic techniques offer little as a reliable diagnostic alternative to the lacerating biopsy and histology.

SUMMARY OF THE INVENTION

It is an object of the present invention to provide an apparatus and method for sampling epithelial cells from the anatomy without the pain or injury of lacerational biopsies.

It is a further object of the present invention to provide an apparatus for sampling epithelial tissue in the oral cavity, the vulva, and similar keratinized epithelia.

It is a further object of the present invention to provide a non-lacerating apparatus for readily sampling cells from all levels of a surface epithelial lesion, including the basal, intermediate and superficial layers of the lesion.

It is a further object of the present invention to provide an apparatus for sampling cells from the entire surface of a lesion, to completely sample a suspect lesion which may be multifocal.

Further objects of the invention will become apparent in conjunction with the disclosure herein.

In accordance with the present invention, an apparatus is provided for sampling all types of epithelium, particularly squamous epithelium, from lesions found in the oral cavity, the vaginal cavity, and other similar keratinized epithelia. Further in accordance with the invention, an improved method is provided for testing questionable lesions found in the epithelium of the oral cavity and other body tissues. The method invented involves exerting sufficient pressure in the lesion area with a surface or edge capable of dislodging cells in and under a keratinized layer.

For purposes of this patent application, the prior art scalpel procedure is defined as lacerational, whereas the novel invention herein is non-lacerational and therefore minimally invasive. To the extent that an abrasive brush has characteristics that may cause minor discomfort and/or bleeding, there is substantial difference between the prior art scalpel trauma and the minimal trauma associated with the present invention.

In accordance with the present inventions, focal sampling of questionable lesions of the oral cavity and of similar epithelia is provided using a specialized, stiff-bristled, brush device disclosed herein. By rubbing harder than normal cytological sampling, and using a device which penetrates epithelium but not very deep on each stroke, one can reach to the basement membrane without lacerating. As opposed to the prior art, use of the device allows cell sampling which can readily and consistently produce a transepithelial cytologic sample. That is, by utilizing the invention disclosed herein, cells can readily and consistently be obtained from all levels of the epithelium (basal, intermediate and superficial) of a suspect lesion, thus overcoming the limitation in the prior art of abnormal epithelial cells being inaccessible to cytology for a variety of reasons, including because they are covered by a keratin layer. The resulting cellular sample functionally approximates the cellular sample of a lacerating biopsy device, but is obtained with the ease of a swab application, and without discomfort to the patient. The subject invention therefore makes practical the routine testing of questionable lesions of the oral cavity, thus allowing early detection and treatment of oral cancer and pre-cancer. Furthermore, the invention can be utilized in testing benign neoplasms, a diverse group of inflammatory oral diseases such as pemphigus and lichen planus, oral lesions which represent manifestations of systemic diseases such as nutritional deficiencies and anemia, viral, bacterial, and fungal infections, reactive and traumatic processes, and chromosomal sex determination.

While the preferred embodiment has been described with respect to a brush, the present invention generally describes a method and apparatus for obtaining transepithelial specimens of a body surface. The invention relates to a non-lacerational method and apparatus to obtain such a specimen. The reason one seeks to obtain a transepithelial sample is because suspect cells appearing at the superficial layer of the epithelium originate at the basal layer within the tissue. With respect to the oral cavity, basal cells originate in the general area of the basement membrane separating the epithelial tissue from the tissue below the membrane known as the submucosa. In determining whether or not a patient has a precancerous or cancerous condition, it is important to reach down to the basement membrane and slightly therebelow because metastases may be suspected depending on the cellular architecture existing at just below or at the basement membrane through to the superficial layer.

Alternate ways to obtain such a transepithelial specimen without laceration include electromagnetic, optical, microwave, ultrasound, mechanical and chemical. With regard to chemical, it is possible that the enzyme hyaluronadase could be used since this chemical could separate the epithelium from between the basement membrane. If one could actually obtain the entirety of a transepithelial layer, the cell architecture would be readily apparent, but such an approach would also materially harm the patient. Therefore, obtaining a more limited specimen and collection of cells is what is desired, and the preferred embodiment of using the brush is identified.

In accordance with the present invention, a toroidal or donut shaped brush is provided for cell sampling, as disclosed below. The brush provides a more complete sampling of the epithelium than the brushes of the prior art. In accordance with the present invention, a method is further provided for sampling epithelial cells. According to the method, the brush of the present invention may be rotated against or brushed parallel to, an epithelial surface, to burrow into and deeply sample epithelial cells. A rotation motion or other scrub motion essentially operates to scrub across the lesion thereby causing cells to be lifted from the surrounding tissues and adhere to the bristles of the brush. The structure of the brush and bristles including the stiffness thereof as well as the shape of the bristle tips contribute to the effectiveness of the brushing or scrubbing action in retrieving cells from the transepithelial layers. The shape of the bristle tips is determined by the bristle cutting process. The bristle tips, preferably, have scraping edges.

The tips of the brush and the brush itself may be considered as an assemblage of pentrating edges.

DETAILED DESCRIPTION OF THE INVENTION AND THE PREFERRED EMBODIMENTS

Figure 1:
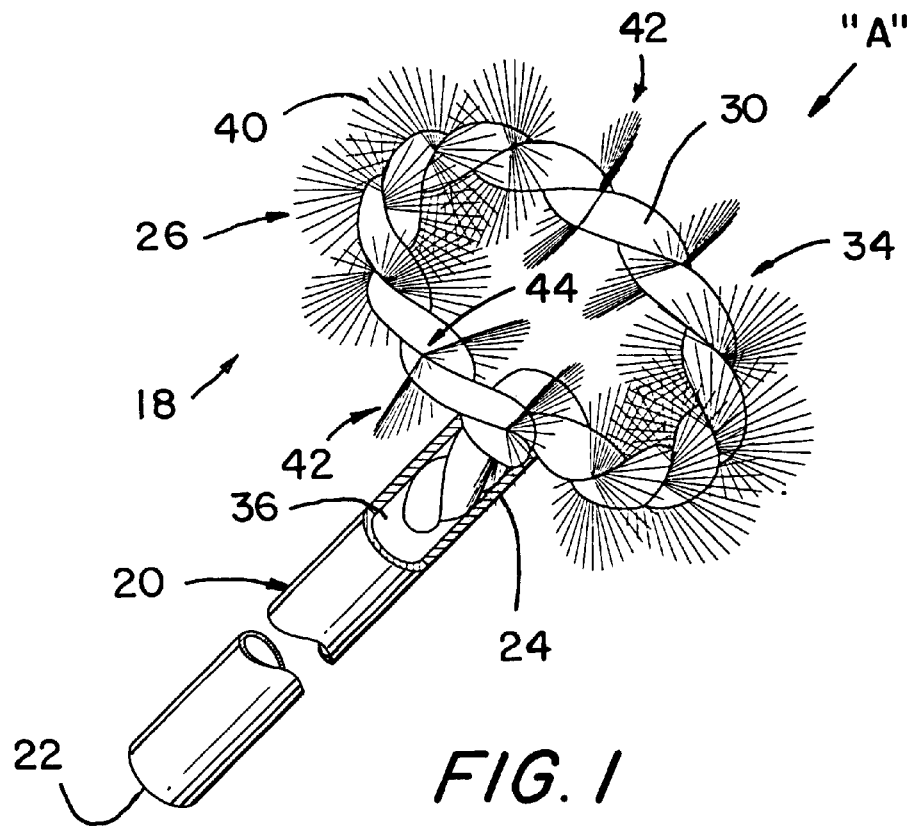
FIG. 1 is a perspective view of an apparatus for sampling epithelial tissue in accordance with the present invention.
Figure 2:
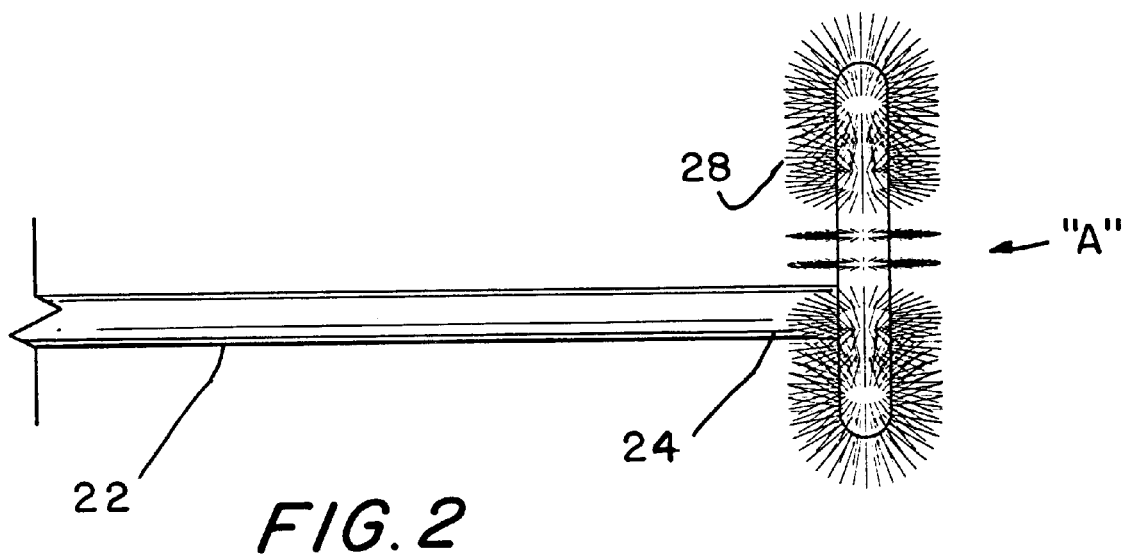
FIG. 2 is a side view of the apparatus for sampling epithelial tissue shown in FIG. 1.
Figure 3:
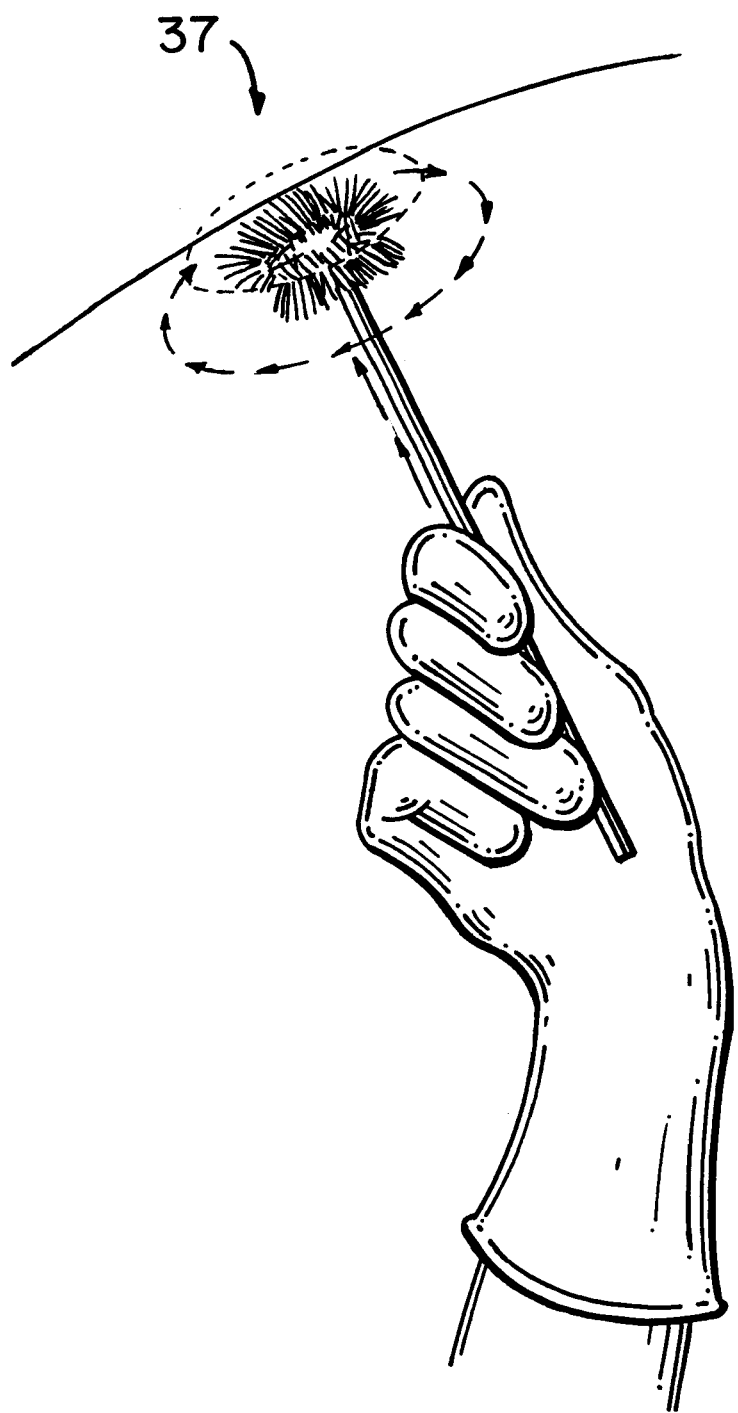
FIG. 3 is a perspective view of using the brush of the present invention to sample a lesion, in accordance with the method of the present invention.
Figure 4:
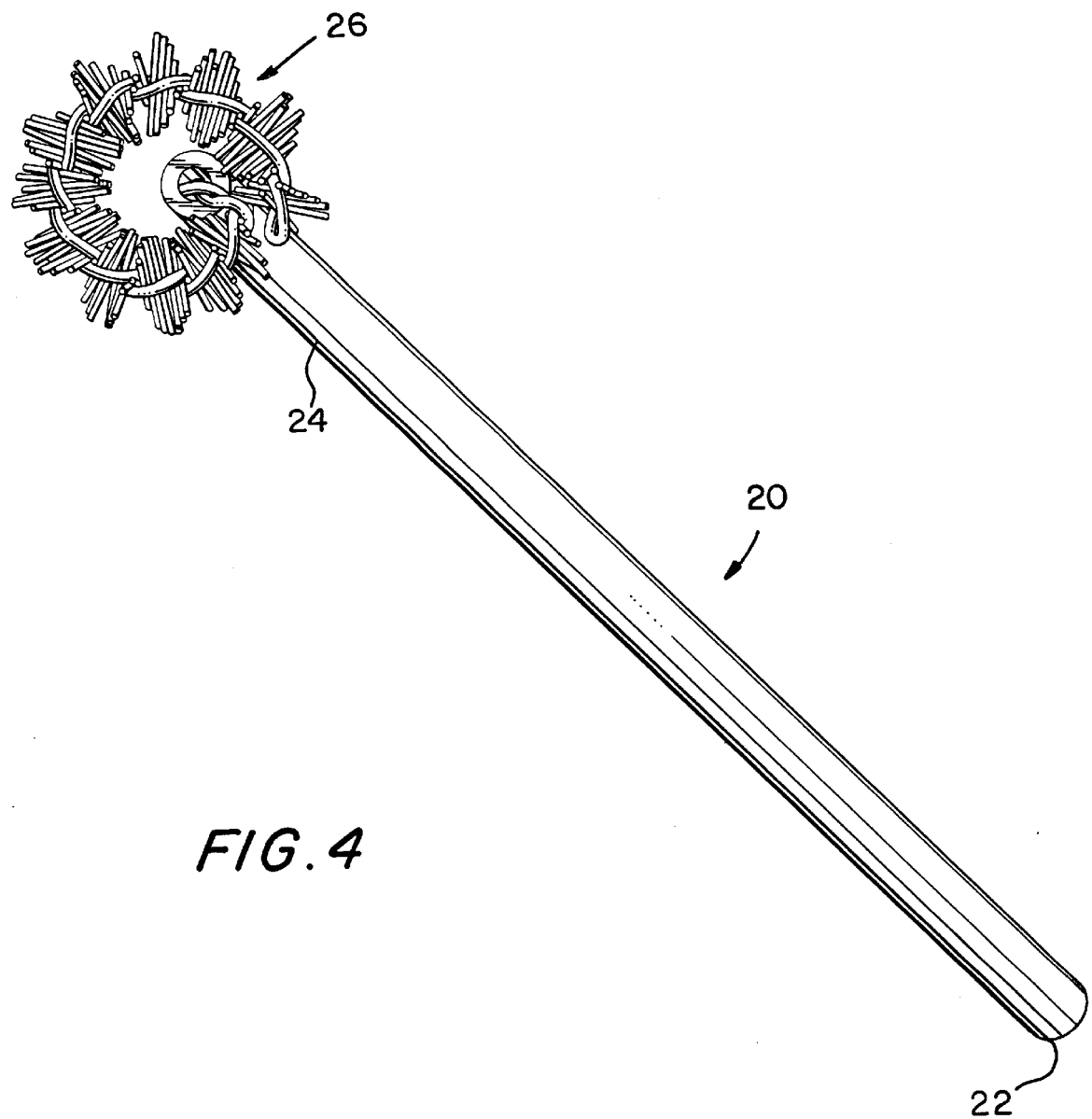
FIG. 4 is an enlarged perspective view of the brush of this invention.
Figure 5:
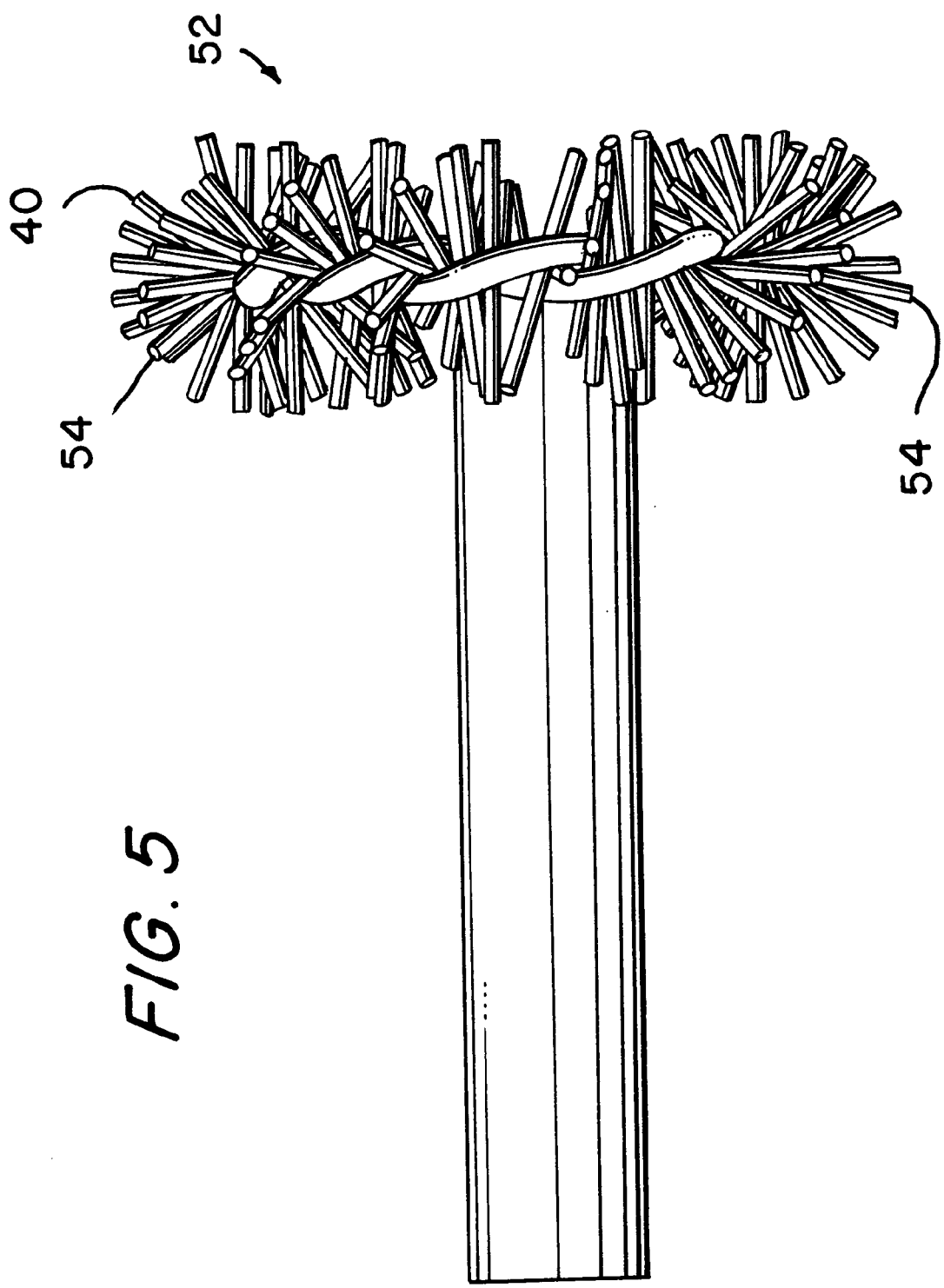
FIG. 5 is a side view of the enlarged view of the brush of this invention shown in FIG. 4.
Figure 6:
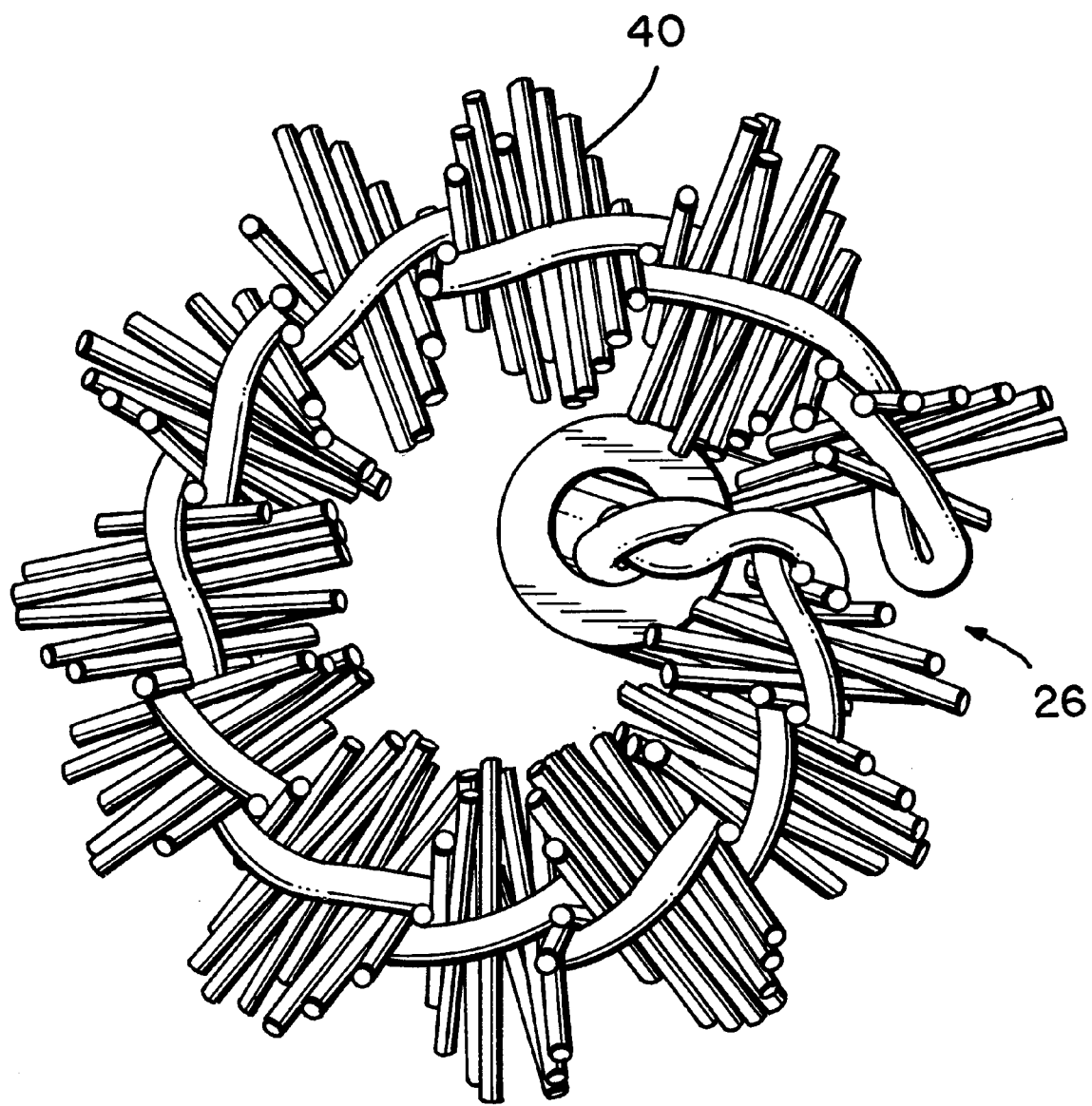
FIG. 6 is an end view showing the bristles of the brush shown in FIG. 4.

FIGS. 1–3 were submitted with the original provisional patent application. FIGS. 4–6 are more detailed and more accurate representations of the brush and bristle structure including its specific construction. Submitted in this detailed description are photographs taken by an electron microscope of the ends of the bristles further illuminating the structural aspects of the bristles which contribute to the effectiveness of the brush in obtaining transepithelial samples.

A preferred embodiment of the invention is provided in FIG. 1. In accordance with the invention, a device 18 is provided which comprises a handle or elongate member 20, having both a proximal end 22 and a distal end 24. In the preferred embodiment, the total length of the device is approximately six inches.

Handle 20 is designed for gripping by a user, and is of a sufficient length to allow the user to manipulate the device within a body cavity from a location just outside the body. In the preferred embodiment, handle 20 is semi-rigid so as to assist in reaching the target tissue notwithstanding difficult angles or narrow passages. In the preferred embodiment, the handle is approximately 5 inches long.

The brush handle can be constructed of a plastic, such as polypropylene, or any other suitable semi-rigid material. The handle can be solid, but is hollow in the preferred embodiment. It is further preferred that handle 20 also have at least one area whose cross-section is substantially circular such that the elongate member may be readily twirled between the thumb and forefinger while pressed against a lesion. Another way to reach areas that are somewhat difficult in the oral cavity would be to hold the handle short and rotate and scrub the side of the brush, rather than its end, against the lesion area. This will also be effective in the brush bristles passing through the transepithelial layers to retrieve cells in the lesion area.

At or around the distal end 24 of the handle or elongate member 20, the device is provided with a brush head 26. Brush head 26 is preferably a substantially toroidal or "donut" shaped brush which presents bristles both towards its end and side, and can be formed from one or more twisted or braided wires, backbone or cables 30. Wires or cables 30 are preferably secured to handle 20 by affixation to backbone or the wire 30 in a recess 36 located in the distal end 24 of the handle. The brush can be formed from conventional twisted wire brush construction. In a preferred embodiment, the total length of the twisted wire is approximately 1.1 inches, with approximately 0.2 inches inserted in the handle, and approximately 0.9 inches exposed as part of the toroid.

Wires or cables 30 are preferably bent to form an incomplete toroid 34 which is perpendicular to the longitudinal axis of handle 20. In other words, toroid 34 preferably defines a circular plane, the plane being provided perpendicular to the longitudinal axis of the handle 20 of brush head 26. Alternatively, a cross-section of the brush forms a nautilus or spiral shape at ninety degrees to the handle or elongate member 20. The brush could be curled into an outward spiral in the same plane. The metallic spine of the brush spirals out in a plane which is perpendicular to the handle. This is more clearly seen in FIGS. 4–6.

Brush head 26 may be integral with handle 20, or may be detachable. It may be a reusable sterilizable or surgical holder. Alternatively, the proximal end 22 of the handle 20 may be detachable from the distal end 24. The detachable portion of the brush may be scored, to easily break away, may be provided with screw threads to screw off the remainder of the device, or so forth. In either embodiment, detachment of either the brush head or of a portion of the handle connected to the brush head, can allow the distal end of the brush, having sampled cells collected therein, to be separated from the proximal end. This allows the handle or the proximal end thereof to be discarded while the distal end of the apparatus is forwarded to the laboratory for analysis. The bristles are also used to collect cells as well as perform the transepithelial activity. For example, the distal portion of the device can be dropped into a transfer solution, while the proximal portion is thrown away.

Brush head 26 is further provided with a plurality of bristles 40. In the preferred embodiment, bristles 40 are approximately 0.25 inches from tip to tip, protrude 0.05–0.2 inches from the toroidal wire and have a stiffness of between 0.04–0.2 lbs/inch. The stiffness is better identified as a cantilever or lateral tip deflection stiffness. Each end of the bristle protrudes a distance of about 0.10 inches from the wire spine. The bristles are approximately 0.006 inches (0.16 mm) thick.

Although in the prior art, the sampling brushes provided have been soft brushes with soft bristles, in the present invention, bristles 40 are specifically made stiff or semi-rigid, going against the teachings of the art. As described above, for example, U.S. Pat. No. 4,759,376 teaches that the bristles of the brush should be relatively soft and should readily bend Likewise, the brush disclosed in U.S. Pat. No. 4,762,133, is also meant to be soft, as is it provided for sampling the exocervix along with the endocervix. This preference heretofore in the art to use a soft brush prevents damage to tissue. While this is generally desirable in the cervix, it is not helpful when the lesions are keratinized, as in the oral cavity.

Moreover, sampling below the superficial layer of the epithelium is not known to have been achieved with prior art brushes. In contrast, in the present invention, it is specifically desired to disrupt the tissue of a lesion and penetrate beneath the superficial layer of the epithelium to sample all three epithelial layers. Whereas the prior art brushes are generally designed for the cervix where no keratin is present, the present brush can penetrate through keratin covered lesions to provide a suitable tissue sample. It may be preferable to have a plurality of scratches or furrows in the tissue from the brush, one of which will penetrate the basement membrane over a substantial area of the lesion. In the present invention, each stroke penetrates a little so that the depth of penetration can be controlled by the appearance of spot bleeding.

Accordingly, in the present invention, bristles 40 of brush head 26 are each stiff or semi-rigid. The bristles are preferably made of Tynex® brand nylon laid in a double layer and have a diameter of between 0.010 cm and 0.022 cm. The Tynex® brand bristles have their own cantilever stiffness which may be at a modulus of 500,000 psi. Preferably, the bristles have a diameter of approximately 0.016 cm and protrude 0.10 inches from the wire spine. Although triple and single row densities may be used, double row density bristles are preferred. A range of protruding lengths of 0.08 to 0.16 inches could be used.

Bristles 40 are preferably provided in a series of arrays 42. As shown in FIG. 1, each array 42 is composed of a series of bristles 40, the bristles extending radially from a center 44, to form each of the arrays 42. At center 44, the end of each bristle 40 is secured within the twisted wire 30 backbone.

Arrays 42 preferably extend around the entire perimeter of toroid 34. In one embodiment, viewing the apparatus head-on, from the perspective "A" in FIGS. 1 or 2, tufts of bristles are evenly arranged around the perimeter of the toroid. Thus, the arrays are arranged at 30 degrees spacings along the twisted wire of the brush head.

The bristles do not form a plane, but rather preferably extend upward from center 44 at an acute angle to wire 30. As a result of this bristle orientation, rotation will result in a degree of bristle abrasion that is effected by the bristles splaying under load. Rotation in the opposite direction will result in abrasion that is greatly accentuated by maximizing the direct piercing of the skin with the stiff bristle ends. While the unique drilling combination of bristle pressure, tip shape, stiffness, brushing and rotation results in provision of the trans-epithelial cytologic sample of the lesion as noted above, rotation in the direction which moderates direct surface piercing by the bristle ends (clockwise, in the case of the preferred embodiment) allows this trans-epithelial cytologic sample to be obtained with minimal discomfort to the patient.

Further, an advantage and feature of this invention achieved with the brush is that a rather large area around the lesion area is subject to the action of the brush which enhances the cell collection process to provide a more effective sampling.

The photographs of FIGS. 12A–12D are electron microscope enlargements of the front edge or tips of the bristles of this invention. The tips of the bristles provide good scraping or cutting surfaces. These scraping or cutting surfaces help to dislodge the cells from the surrounding tissue to be collected on the bristles. The sharp edges do not dig too deeply into the epithelial tissue and avoid severe injury.

Figure 7:
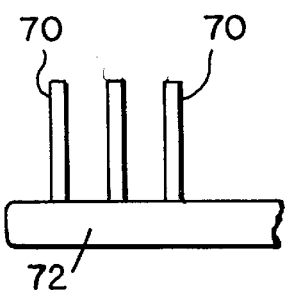
FIGS. 7 and 8 are side views of alternate structures for the bristles showing the bristle tips.
Figure 8:
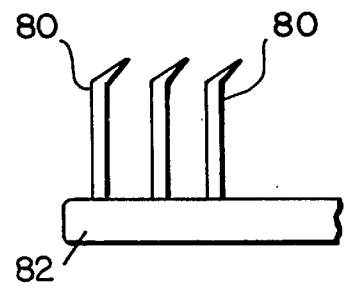
Figure 9:
FIG. 9 is a side view of an alternate structure for abrading.

FIGS. 7 and 8 are cross sectional views of alternate brush structures with the front edges of the bristles 70 being squared as in FIG. 7 or "file card wire brush type edges" 80 which are aligned as in FIG. 8. The squared britles of FIG. 7 form non-penetrating scraping edges and even generate negative rake angles when the bristles bend over. Both brushes are attached to handles 72 and 82 respectively. It is preferable to have a large number of such bristles to spread the pressure as the brush structure is being used. An alternative structure in FIG. 9 illustrates a plurality of small rigid scrapers 90 which could be employed at the edge of the brush and attached to handle 92. Such scrapers would extend from handle 92.

Figure 10A:
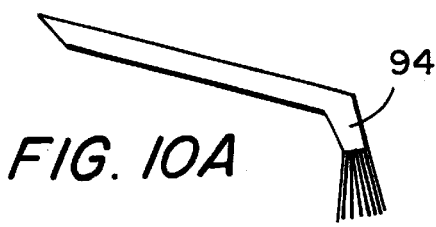
FIGS. 10A and 10B are alternate brush structures.
Figure 10B:
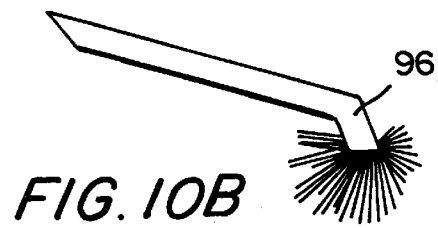
Figure 12A:
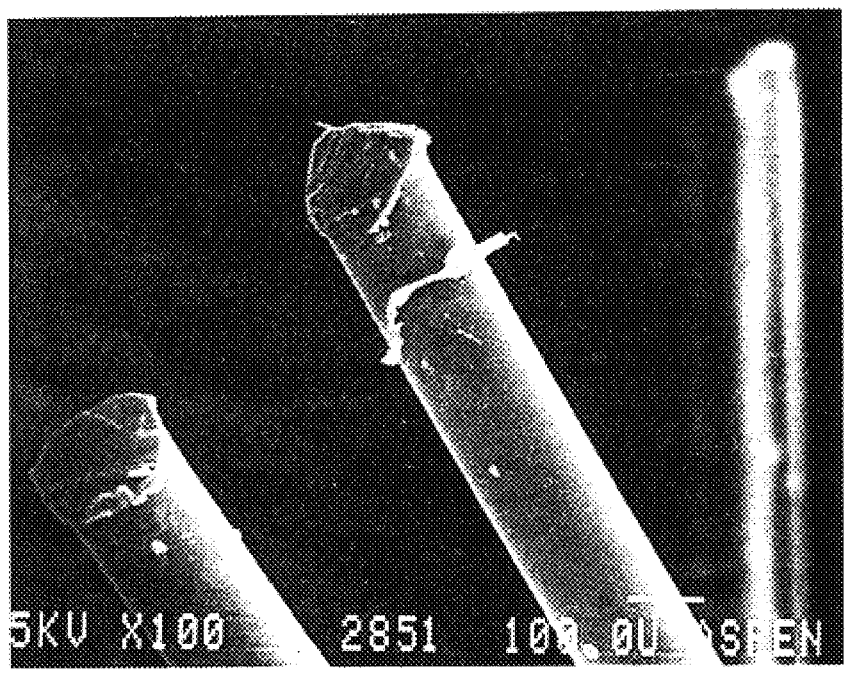
FIGS. 12A and 12B are electron microscopic enlargements of the blunt or square cut bristle ends.
Figure 12B:
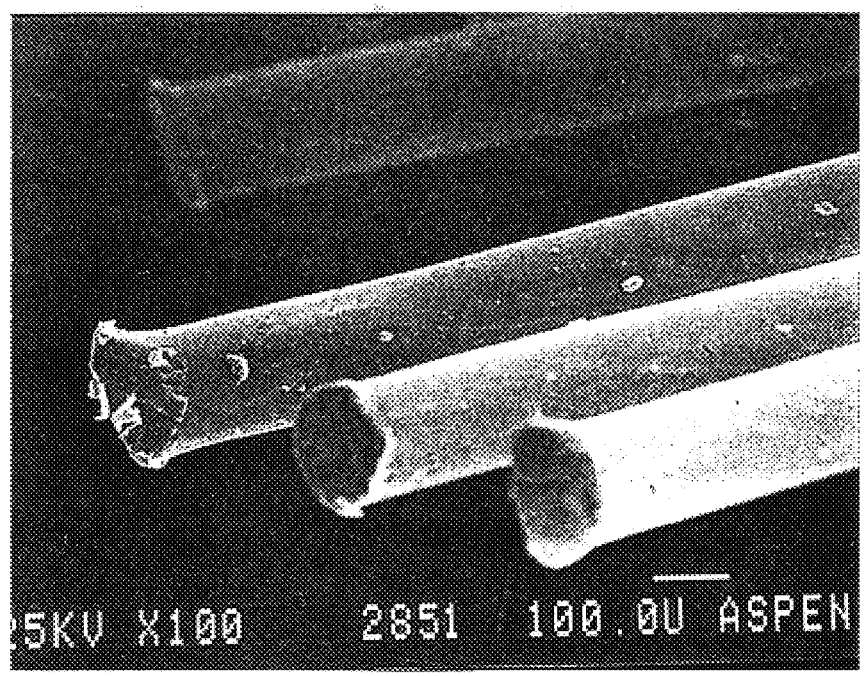
Figure 13A:
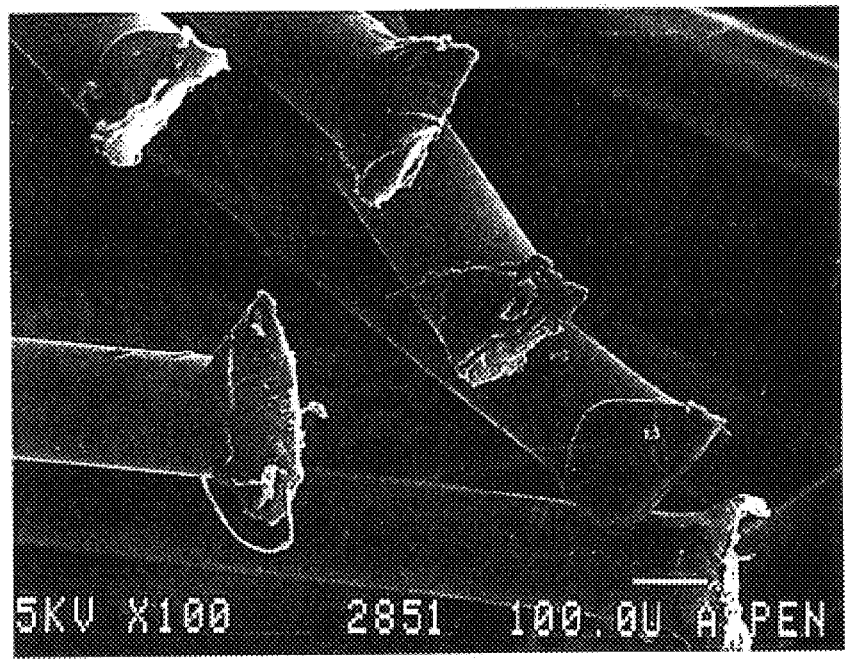
FIGS. 13A and 13B are electron microscopic enlargements of the wedge or chisel cut bristle ends.
Figure 13B:
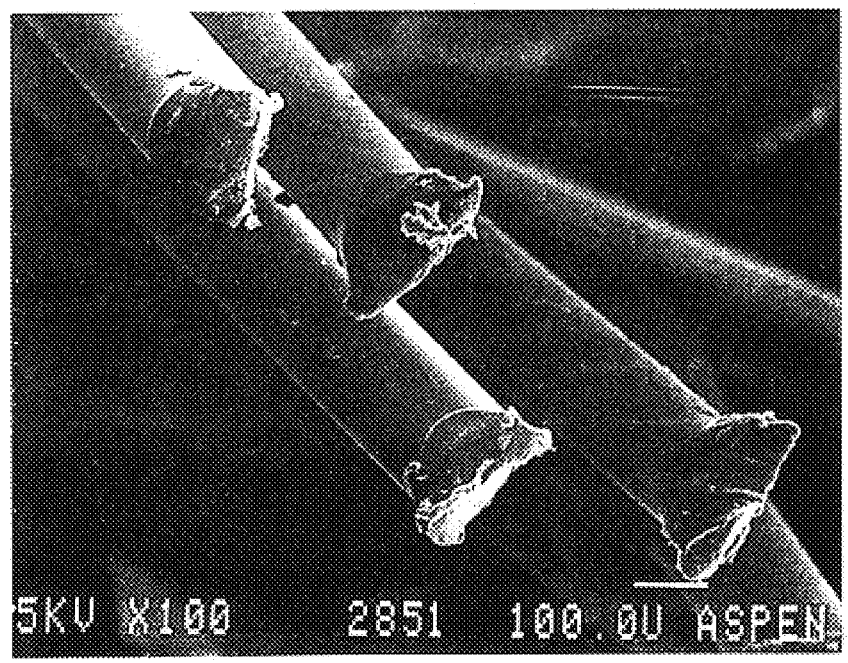

FIGS. 10A or 10B illustrate conventional brush arrangements 94 and 96 adjoined to a handle allowing end or side pressure. These brushes can be rubbed back and forth to dislodge and remove the cells for their collection. A plurality of different abrasive materials such as finely ribbed or bumpy materials could be employed, where the protrusions may be shaped with edges to apply highly localized pressure, and catch against cell clusters rather than sliding over them. FIGS. 4 through 6 are respectively perspective side and end views of an enlargement of the brush of this invention. The bristles 40 are seen collected and captured in the metallic wire 30 to form a relatively irregular surface although the side view in FIG. 5 illustrates that the front plane 52 of the brush head 26 presents a relatively flat planar surface. In use, only the outer front plane 52 or the edge planes 54 of the brush head will be used to retrieve cells from the epithelial tissue structure. The following is a list of alternative models for materials which could sample cells. Such materials would generally not be introduced into a patient's mouth.

| Abrasive Materials/Tools | |
| --- | --- |
| brillo pad, fine steel wool pad gauze, sterile pads, file, pumice, sponges, loofah | Brushes |
| velcro, hook and loop cotton swab with salt, steel wool or glass fiber cat tongue, shark skin powder/abrasive other types of abrasive put on a flexible backing | radial Dremel brush bristle brush bristles that poke out slightly, similar to 5 o'clock shadow, (light beard) |
| | Other |
| Scraper or File Tools | abrasion other test methods, wear |
| Metal or plastic blades, file molded out of plastic toothpick two pronged tool, one to break layer, one with pad to absorb triangular shaped wire loop, dental scraper dental burr, regular burr fresnel lens like instrument (fine molded ridges) plastic helix file made out of cuttle fish bone sintered glass, aerator stone | testing rubber ball to squeeze out material onto slide small pads that have adhesive on them that can be pulled off chemical process (weak acids) |

The present invention allows for limited space between the points of abrasive contact upon brush rotation, while maintaining enough separation between the bristles to trap a clinically effective amount of cells. The length of the stiff bristles of the brush may also vary but is similarly balanced between: 1) the requirement to keep the bristles stiff enough to grind the tissue into its cellular components during rotation; 2) the requirement that the bristles be long enough to trap the removed cells with these extending 0.1 inch from the wire toroid; and 3) soft enough to bend.

As shown in FIG. 3, according to the method of the present invention, the flat distal end of the handle of the brush is placed directly on the site of the suspect lesion 37. The stiff dense bristles are then pushed firmly against the lesion site while the handle is simultaneously rotated clockwise at least once, and preferably several times about its axis. The metal or twisted wire of the brush head assists in the application of pressure to the epithelial surface. The trained user will continue rubbing until pinpoint bleeding is observed.

Rotation of the bristles against the lesion results in the scraping detachment of cells from multiple layers of the epithelium. The detached cells become collected between the stiff bristles and are trapped there. These cells can then be inspected by a suitable laboratory.

The method of the present invention is particularly advantageous due to the fact that, as no laceration of the epithelium is required, the discomfort experienced by the patient is considerably less than that of a surgical biopsy, and is generally minimal. Further, this invention effects sampling over a large area.

The method of the present invention is in contrast to the method of the prior art, in which the technique has been to "sweep" the soft bristles of a brush or other non-abrasive instrument over and across the surface of a lesion. In the present invention, the stiff bristles are pressed down and brushed or rotated into a lesion of potential concern to penetrate or "drill" into the lesion. This drilling presents the ability to thoroughly sample all layers of the epithelium without the necessity of performing a surgical laceration. Specifically, the preferred embodiment's unique combination of: 1) sufficient manual pressure transferred directly by the handle of the device to the interface between the flat surface of the brush and the surface of the lesion; 2) keeping the sharp bristle edge in contact with the epithelium and, 3) rotation of the device, provide this superior "drilling" action in the epithelium which has previously been unknown in the art of cytology. It is this unique drilling action which results in the unique and improved ability of the subject invention to provide a cytological sample of a keratinized lesion which contains cells from all layers of the underlying epithelium. As such, the cytologic sample obtained by the present invention is the functional equivalent of the tissue section type of sample taken by the prior art lacerating biopsy technique, and yet is obtained without the patient discomfort, scarring, and other difficulties potentially associated with a lacerating biopsy.

Moreover, in addition to avoiding patient discomfort and scarring, the present invention poses yet a further advantage over the prior art lacerating technique. In the present invention, a sample can be obtained from the entire surface of a multifocal lesion to provide a broad sample of cells from the entire lesion for further testing. In contrast, in the prior art incision surgical biopsy a tissue core is taken of only a section of a lesion to test the lesion for malignancy. Accordingly, due to the fact that the particular portion of the lesion sampled by the surgical technique may be benign, while a non-sampled portion of the lesion may be malignant, false negatives may potentially occur. The present invention's broad sampling of a lesion avoids this potential problem. Thus, it is further preferred, in accordance with the method, that the brush be rotated over the entire surface of a lesion, and not just a portion thereof, to ensure that sampling is as thorough as possible in the event that the lesion is multifocal. In this manner, the invention avoids the disadvantages of the prior art.

Figure 11:
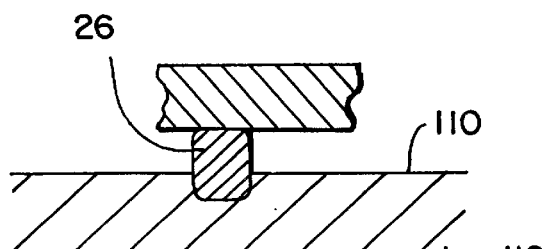
FIG. 11 is a sectional view of the tissue in the oral cavity showing the brush penetrating the basement membrane and reaching to the submucosa.

FIG. 11 is a cross-section of the basement membrane 110 and submucosa 112 therebelow with the scraping or abrading unit 26 shown penetrating slightly below the basement membrane. Such penetration is preferred to obtain and harvest cells for analysis.

In a clinical study, a group of patients with visible oral lesions were tested using cytological samples obtained with the preferred embodiment of the subject invention. In 93% of cases the subject invention resulted in a trans-epidermal sample of the suspect lesion. That is, in 93% of samples taken cells were obtained from the basal, intermediate, and superficial layers of the oral epidermis. In a subset of these transepithelial specimens obtained with the subject invention a matching lacerating biopsy was also performed of the same lesion. In all histological confirmed positive cases in that subset, correlation between the cytological smear diagnosis obtained with the subject invention and the histological diagnosis obtained with a lacerating biopsy was perfect for the detection of pre-cancer and cancer. These results were achieved using the subject invention without a single report of patient discomfort, the requirement of any form of local anesthetic, or scarring as would be expected with the lacerating biopsy technique.

Use of the subject invention is not limited to the oral cavity, but extends to other epithelia where a lesion requiring diagnosis may be observed, where exfoliation of cells is limited by the presence of keratin or other factors, and where an alternative to a lacerating biopsy is desired. Cytological testing of observed lesions of the vulva is one such example of an alternate potential use of the subject invention.

Having described this invention with regard to specific embodiments, it is to be understood that the description is not meant as a limitation since further modifications and variations may be apparent or may suggest themselves to those skilled in the art. It is intended that the present application cover all such modifications and variations as fall within the scope of the appended claims.

What is claimed is:

1. Apparatus to obtain cells in epithelial tissue of the body comprising:
   transepithelial non-lacerational sampling apparatus to collect cells from at least two layers of said epithelial tissue, said transepithelial non-lacerational sampling apparatus comprising a brush, said brush comprising bristles having sufficient stiffness to penetrate at least said two layers of said epithelial tissue.

2. Apparatus to obtain cells in epithelial tissue of the body according to claim 1, wherein said bristles collect cells from three layers of said epithelial tissue, said three layers comprising superficial, intermediate and basal layers, said basal layer separated from the submucosa by a basement membrane.

3. Apparatus to obtain cells in epithelial tissue of the body according to claim 2, wherein said bristles of said brush have sufficient stiffness to penetrate said basement membrane and reach said submucosa.

4. A transepithelial non-lacerational sampling apparatus according to claim 2, wherein said brush comprises a handle, said handle comprises a distal and a proximal end, said brush is connected to said distal end, said bristles of said brush forming an abrasive surface.

5. Apparatus to obtain cells as set forth in claim 1, wherein said brush comprises a handle and a head portion, said head portion comprising bristles.

6. A transepithelial non-lacerational sampling apparatus according to claim 5, wherein said handle comprises a cylinder.

7. A transepithelial non-lacerational sampling apparatus according to claim 5, wherein said head portion comprises bristles directed outwardly from said head portion.

8. A transepithelial non-lacerational sampling apparatus according to claim 7, wherein said handle has a distal and a proximal end, said head portion comprises bristles directed radially outwardly from the distal end of said handle.

9. Apparatus as set forth in claim 5, wherein said bristles have a tip stiffness, and wherein the tip stiffness of each bristle is between 0.04 and 0.2 lbs/inch.

10. Apparatus as set forth in claim 9, wherein said bristles have a tip stiffness, and wherein said bristles protrude between 0.05–0.2 inches.

11. Apparatus as set forth in claim 5, wherein said bristles have a tip stiffness, and wherein said bristles protrude between 0.05–0.2 inches.

12. A transepithelial non-lacerational sampling apparatus to harvest cells in an oral cavity from the epithelial tissue, said epithelial tissue comprising superficial, intermediate and basal layers, and a basement membrane located between the basal layer and the submucosa, said non-lacerational sampling apparatus comprising means to traverse said superficial, intermediate and basal layers and to collect cells from said three layers.

13. A transepithelial non-lacerational sampling apparatus according to claim 12, wherein said means to traverse said three layers comprises sufficient stiffness to traverse said basement membrane and reach into said submucosa.

14. A transepithelial non-lacerational sampling apparatus according to claim 4, wherein said brush comprises a handle and a head portion, said head portion comprising bristles.

15. A transepithelial non-lacerational sampling apparatus according to claim 14, wherein said handle comprises a cylinder.

16. A transepithelial non-lacerational sampling apparatus according to claim 14, wherein said head portion comprises bristles directed outwardly from said head portion.

17. A transepithelial non-lacerational sampling apparatus according to claim 16, wherein said handle has a distal and a proximal end, said head portion comprises bristles directed radially outwardly from the distal end of said handle.

18. A transepithelial non-lacerational sampling apparatus according to claim 12, wherein said handle comprises a distal and a proximal end, further comprising wires connected to and extending from said distal end, said bristles held by said wires to form brushing surfaces at the tips of said bristles, said brushing surfaces abrading said epithelial tissue.

19. A transepithelial non-lacerational sampling apparatus according to claim 18, wherein the tip stiffness of each bristle is between 0.04 and 0.2 lbs/inchh.

20. A transepithelial non-lacerational sampling apparatus according to claim 19, wherein said bristles protrude by between 0.05–0.2 inches from the wires in which said bristles are held.

21. A transepithelial non-lacerational sampling apparatus according to claim 18, wherein said wires form a toroid which is substantially perpendicular to the axis of said handle.

22. A transepithelial non-lacerational sampling apparatus according to claim 21, wherein said brush is in the form of a spiral shape substantially perpendicular to the axis of said handle.

23. A transepithelial non-lacerational sampling apparatus according to claim 12, wherein said bristles comprise tips, wherein said tips comprise scraping edges.

24. A transepithelial non-lacerational sampling apparatus according to claim 12, wherein said brush comprises a handle, said handle comprises a distal and a proximal end, said brush is connected to said distal end, said bristles of said brush forming an abrasive surface.

25. A transepithelial non-lacerational sampling apparatus according to claim 12, wherein said brush has a round head, said bristles being stiff.

26. A method to collect cells in epithelial tissue of the body comprising:

passing a transipithelial non-lacerational sampling means through the epithelial tissue to collect cells from at least two layers of said epithelial tissue.

27. A method to collect cells in epithelial tissue of the body according to claim 26, wherein said transepithelial non-lacerational sampling means collects cells from three layers of said epithelial tissue, said three layers comprising superficial, intermediate and basal layers.

28. A method to collect cells in epithelial tissue of the body in which a basement membrane is located below said basal layer according to claim 27, wherein said transepithelial non-lacerational sampling means penetrates said basement membrane.

29. A method to collect cells in epithelial tissue of the body according to claim 28, wherein said transepithelial sampling means is rotated and drilled into said tissue.

30. A method to collect cells in epithelial tissue of the body according to claim 28, wherein said transepithelial sampling means is moved substantially perpendicularly into said tissue.

31. A method to collect cells in epithelial tissue of the body according to claim 27, wherein said epithelial tissue comprises oral epithelial tissue.

32. A method to collect cells in epithelial tissue of the body according to claim 27, further comprising abrading the epithelial tissue to collect cells.

33. A method to collect cells in epithelial tissue of the body according to claim 32, wherein said epithelial tissue has a keratinized layer and said cells are collected from beneath said keratinized layer.

34. A method to collect cells in epithelial tissue of the body according to claim 26, wherein said epithelial tissue comprises oral epithelial tissue.

35. A method to collect according to claim 26, further comprising abrading the epithelial tissue to collect cells.

36. A method to collect cells in epithelial tissue of the body according to claim 26, wherein said method comprises the step of exerting sufficient pressure on a scrubbing surface in contact with said epithelial tissue to dislodge cells.

37. Apparatus to obtain cells in epithelial tissue of the body comprising:

transepithelial non-lacerational sampling apparatus to collect cells from at least two layers of said epithelial tissue, said transepithelial non-lacerational sampling apparatus comprising an assemblage of penetrating edges to penetrate at least said two layers of said epithelial tissue.

38. Apparatus to obtain cells in epithelial tissue of the body according to claim 37, wherein said assemblage of penetrating edges collect cells from three layers of said epithelial tissue, said three layers comprising superficial, intermediate and basal layers, said basal layer separated from the submucosa by a basement membrane.

39. Apparatus to obtain cells in epithelial tissue of the body according to claim 38, wherein said assemblage of penetrating edges penetrates said basement membrane and reach said submucosa.

* * * * *